(12) United States Patent
Bavari et al.

(10) Patent No.: US 7,879,330 B2
(45) Date of Patent: Feb. 1, 2011

(54) ANTIBODIES AGAINST TYPE A BOTULINUM NEUROTOXIN

(75) Inventors: Sina Bavari, Frederick, MD (US); Edna R. Torres Melendez, Frederick, MD (US); Frank J. Lebeda, Pharmont, MD (US)

(73) Assignee: The United States of America as represemted by the Secretary of the Army, Washington, DC (US)

( * ) Notice: Subject to any disclaimer, the term of this patent is extended or adjusted under 35 U.S.C. 154(b) by 823 days.

(21) Appl. No.: 11/368,727

(22) Filed: Mar. 6, 2006

(65) Prior Publication Data

US 2006/0177881 A1    Aug. 10, 2006

Related U.S. Application Data

(62) Division of application No. 10/655,450, filed on Sep. 4, 2003, now Pat. No. 7,049,085, which is a division of application No. 09/465,276, filed on Dec. 16, 1999, now Pat. No. 6,667,158.

(60) Provisional application No. 60/112,632, filed on Dec. 17, 1998.

(51) Int. Cl.
  *G01N 33/554*  (2006.01)
  *C07H 21/04*  (2006.01)
  *C12P 21/06*  (2006.01)
  *C07K 16/12*  (2006.01)

(52) U.S. Cl. ............... 424/164.1; 530/388.1; 530/388.2; 530/388.4; 530/350; 424/167.1; 435/7.1; 435/7.32

(58) Field of Classification Search .................. None
See application file for complete search history.

(56) References Cited

PUBLICATIONS

Bavari et al. (Vaccine Nov. 1998, vol. 16, No. 19 pp. 1850-1856).*

* cited by examiner

*Primary Examiner*—Robert A Zeman
(74) *Attorney, Agent, or Firm*—Elizabeth Arwine

(57) ABSTRACT

Antibodies for binding epitopes of BoNT/A and hybridomas which produce such antibodies are described. The antibodies of the present invention can be used in a method for detecting BoNT/A in a sample and/or in a method for purifying BoNT/A from an impure solution. In addition, the antibodies can be used for passive immunization against BoNT/A intoxication or as intoxication therapy. Another aspect of the invention is a kit for detecting BoNT/A in a sample.

9 Claims, 10 Drawing Sheets

Figure 2.

| | |
|---|---|
| | SEB-2Ag |
| ׀ | 6E10-10 |
| ׀ | 6E10-8 |
| ׀ | 6E10-5 |
| ׀ | 6E10-4 |
| ׀ | 6E9-4 |
| ׀ | 6E9-3 |
| ׀ | 6E9-1 |
| ׀ | 6C2-4 |
| ׀ | 6B2-2 |
| ׀ | 4A2-4 |
| ▼ | 4A2-2 |

200 — 97 — 68 — C-fragment 43 — 29 — 18 —

Figure 3a.

Kinetics of Interaction of BoNT/A Hc with Captured MoAb 6E9-4

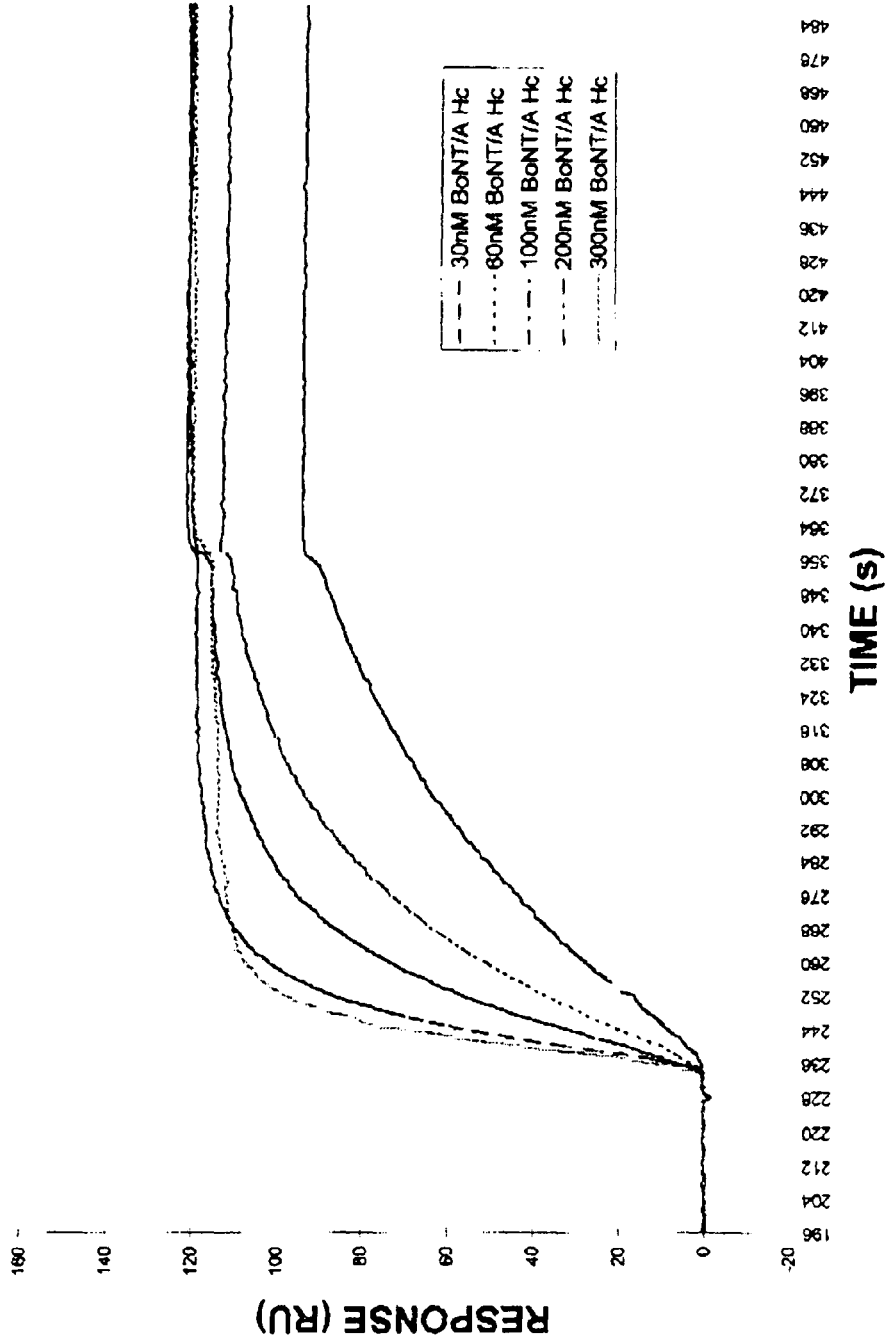

Figure 5.

Epitope Map of BoNT/A mAbs

SEQUENCE LISTING

<160> NUMBER OF SEQ ID NOS: 4

<210> SEQ ID NO 1
<211> LENGTH: 141
<212> TYPE: PRT
<213> ORGANISM: Botulinum neurotoxin type A
<220> FEATURE:

<400> SEQUENCE: 1

```
Leu Asn Ser Ser Leu Tyr Arg Gly Thr Lys
                 5                   10

Phe Ile Ile Lys Lys Tyr Ala Ser Gly Asn
                 15                  20

Lys Asp Asn Ile Val Arg Asn Asn Asp Arg
                 25                  30

Val Tyr Ile Asn Val Val Val Lys Asn Lys
                 35                  40

Glu Tyr Arg Leu Ala Thr Asn Ala Ser Gln
                 45                  50

Ala Gly Val Glu Lys Ile Leu Ser Ala Leu
                 55                  60

Glu Ile Pro Asp Val Gly Asn Leu Ser Gln
                 65                  70

Val Val Val Met Lys Ser Lys Asn Asp Gln
                 75                  80

Gly Ile Thr Asn Lys Cys Lys Met Asn Leu
                 85                  90

Gln Asp Asn Asn Gly Asn Asp Ile Gly Phe
                 95                  100

Ile Gly Phe His Gln Phe Asn Asn Ile Ala
                 105                 110

Lys Leu Val Ala Ser Asn Trp Tyr Asn Arg
                 115                 120

Gln Ile Glu Arg Ser Ser Arg Thr Leu Gly
                 125                 130

Cys Ser Trp Glu Phe Ile Pro Val Asp Asp
                 135                 140

Gly
```

-continued

```
<210> SEQ ID NO 2
<211> LENGTH: 25
<212> TYPE: PRT
<213> ORGANISM: Botulinum neurotoxin type A
<220> FEATURE:

<400> SEQUENCE: 2

Gly Thr Lys Phe Ile Ile Lys Lys Tyr Ala
                5                   10

Ser Gly Asn Lys Asp Asn Ile Val Arg Asn
                15                  20

Asn Asp Arg Val Tyr
                25

<210> SEQ ID NO 3
<211> LENGTH: 25
<212> TYPE: PRT
<213> ORGANISM: Botulinum neurotoxin type A
<220> FEATURE:

<400> SEQUENCE: 3

Gly Ile Thr Asn Lys Cys Lys Met Asn Leu
                5                   10

Gln Asp Asn Asn Gly Asn Asp Ile Gly Phe
                15                  20

Ile Gly Phe His Gln
                25

<210> SEQ ID NO 4
<211> LENGTH: 25
<212> TYPE: PRT
<213> ORGANISM: Botulinum neurotoxin type A
<220> FEATURE:

<400> SEQUENCE: 4

Ala Leu Asn Asp Leu Cys Ile Lys Val Asn
                5                   10

Asn Trp Asp Leu Phe Phe Ser Pro Ser Glu
                15                  20

Asp Asn Phe Thr Asn
                25
```

ANTIBODIES AGAINST TYPE A BOTULINUM NEUROTOXIN

This application is a division of application Ser. No. 10/655,450, filed Sep. 4, 2003, now U.S. Pat. No. 7,049,085, which is a divisional of U.S. Ser. No. 09/465,276, filed Dec. 16, 1999, now U.S. Pat. No. 6,667,158, which claims the benefit of U.S. Provisional 60/112,612, filed Dec. 17, 1998.

Anaerobic bacterium *Clostridium botulinum* produces seven immunologically distinct but structurally similar botulinum neurotoxins (BoNTs) designated BoNT/A-G that are associated with foodborne, infant, and wound botulism (Montecucco and Schiavo, 1994, *Mol. Microbiol.* 13, 1-8; Simpson, 1981, *Pharmacol. Rev.* 33, 155-188). Due to their unique properties, botulinum neurotoxins (BoNTs) have been used to treat a variety of human disorders involving voluntary muscles. BoNT/A was approved in 1989 by the Food and Drug Administration for the treatment of ocular disorders such as strabismus. It has also been used in the treatment of spasmodic torticollis, limb dystonias, vocal disorders, cerebral palsy, gastrointestinal disorders, and tremors (Schantz and Johnson, 1997, *Perspectives in Biology and Medicine* 40, 317-327). Interestingly, BoNT has been found to relieve pain and other syndromes associated with the autonomic nervous system. Injections of BoNT have been shown to induce sweating in certain individuals and relieve migraine headache pain in other individuals. The toxin is known to disrupt the mechanism associated with the release of neuronal substances or neuronal peptides. Besides having the capacity to provide relief from a variety of human diseases, BoNTs also pose a threat as a neurotoxic biological agents.

Following synthesis, highly active neurotoxin generated by proteolytic cleavage of the CNTs (clostridial neurotoxins). The active neurotoxin composed of two main chaines that are connected via a disulfide linkage. The location of the enzymatic subunit of the CNTs has been mapped to the smaller N terminal chain (50-kDa), while the binding and translocation motifs are located within the larger chain (a 100-kD heavy (H) chain). The 50-kD carboxyl-terminal fragment of the H chain (HC) have been postulated to be the receptor binding subunit of the toxin and is thought that this fragment plays a crucial role to direct and pass the enzymatic portion of the CNT accross the vesicle membrane. The zinc-endopeptidase catalytic domain of the toxin resides in the 50 kDa N-terminal portion of the active protein. Upon entry into the cells BoNT works at the neurojunction by rendering key neuronal proteins associated with the release of acetyl-choline inactive (Montecucco and Schiavo, 1994, supra; Blasi et al., 1993, *Nature* 365, 160-163). Very recently, the structure of BoNT/A was solved and showed substantial homology among the structure of the C-terminal binding domain of BoNT/A and Tetanus (Lacy et al., 1998, *Nature Struct. Biol.* 5, 898-902; Umland et al., 1998, *Nature Struct. Biol.* 4, 788-792). Unlike the translocation domain of other toxins, the protein fold seen in BoNT/A translocation domain contains a kinked pair of α-helices and a 54 residue that wraps around the enzymatic domain similar to a "belt" (Lacy and Stevens, 1998, *Curr. Opin. Struct. Biol.* 8, 778-784). The role that the "belt" plays in toxicity of BoNT has not been studied. However, it may play an important role during translocation and cleavage of the substrates.

Although all CNTs are zinc-dependent endopeptidases, they differ in substrate specificity, substrate cleavage-site location, and their sites of action within the central nervous system (Lacy et al., 1998, supra). For example, BoNT serotypes A and E cleave SNAP-25 (synaptosome-associated protein of 25 kDa), while other CNTs cleave syntaxin or synaptobrevin. BoNTs inhibit cholinergic vesicle docking at neuromuscular presynaptic nerve endings and cause potentially fatal flaccid paralysis, whereas TeNT (tetanus neurotoxin) is transported in a retrograde manner to the spinal cord, resulting in spastic paralysis and death (Montecucco and Schiavo, 1994, supra).

SUMMARY OF THE INVENTION

Probably due to unusually high toxicity of BoNTs, previous attempts to produce large numbers of high affinity neutralizing monoclonal antibodies (MAbs) against these neurotoxins have been unsuccesful. We reasoned because immunization with non-toxic binding fragment of BoNT/A can induce protective immunity in mice, then it should be possible to generate neutralizing antibodies using this approach. We report herein that immunization with BoNT/A-Hc allowed the generation of MAbs recognizing both the whole BoNT/A and BoNT/A Hc. We characterized these antibodies in detail, demonstrated biochemical detection of BoNT/A and its binding fragment. We used, neutralizing MAbs directed against the BoNT/A-Hc, in combination with theoretically derived predictions of secondary and solvent accessibility of the residues within the BoNT/A-Hc, to locate the principle protective antigenic determinants (PPDs) of BoNT/A-Hc. Binding of the neutralizing MAbs to overlapping truncated recombinant polypeptides corresponding to BoNT/A-Hc were examined. In addition, we tested MAb recognition of two synthetic 25-mer peptides, whose sequences correspond to predicted solvent-exposed loops within the C-terminal end of the BoNT/A-Hc. Finally, we examined the ability of these peptides to elicit antibody production and to determine whether the resultant antibodies protected the immunized mice from BoNT/A challenge. From these experiments, we identified two regions within the Hc that may contribute to a neutralizing epitope. Because of their ability to neutralize BoNT/A, they could be used for mapping binding sites of the toxin, for competitive-based ELISA to predict immunity following vaccination, identify protective epitopes, and they may be important tools for therapeutic purposes.

Therefore, it is one object of the present invention to provide protective antibodies against BoNT/A. The antibodies of the present invention can be monoclonal or polyclonal antibodies. The present invention also pertains to hybridomas producing antibodies, such as 4A2-2, 6B2-2, and 6C2-4, which bind to an epitope of BoNT/A.

It is another object of the present invention to provide a method of purifying BoNT/A from an impure solution containing BoNT/A. The method involves contacting the impure solution with an antibody which binds an epitope of BoNT/A, allowing the antibody to bind to BoNT/A to form an immunological complex, and separating the complex from the impure solution. The method of purification can further comprise separating the BoNT/A from the antibody and recovering the BoNT/A. In one embodiment, the separation is conducted by contacting the immunological complex with a saturating amount of peptide comprising the epitope recognized by the antibody of the immunological complex.

The present invention still further pertains to a method for detecting BoNT/A in a sample. The method involves contacting the sample with an antibody which binds an epitope of BoNT/A, allowing the antibody to bind to BoNT/A to form an immunological complex, and detecting the formation of the immunological complex and correlating presence or absence of the immunological complex with presence or absence of BoNT/A in the sample. The sample can be biological, environmental, or a food sample.

Yet another aspect of the present invention is a kit for detecting BoNT/A in a sample. The kit includes a container holding an antibody which binds to an epitope of BoNT/A and instructions for using the antibody for the purpose of binding to BoNT/A to form an immunological complex and detecting the formation of the immunological complex such that presence or absence of the immunological complex correlates with presence or absence of BoNT/A.

In still another aspect of the invention is provided a method for identifying the principal protective antigenic determinant of an antigen. The method includes making neutralizing antibodies using the complete antigen, reacting the neutralizing antibodies to different overlapping fragments encompassing the complete antigen, identifying a fragment of the antigen to which most neutralizing antibodies bind, narrowing the region containing the determinant by reacting the neutralizing antibodies to smaller regions of the identified fragment, and identifying the regions to which the neutralizing antibodies bind as the principal protective antigenic determinant.

In yet another aspect of the invention is provided BoNT/A-Hc peptides which have been found to be part of the principal protective antigenic determinants identified as SEQ ID NO:1 and SEQ ID NO:2. The peptides can be used singly or in combination, or the peptide sequences can be combined to produce one sequence and used as one peptide. These peptides may be useful as immunogens, and as a vaccine for protecting against BoNT/A intoxication.

BRIEF DESCRIPTION OF THE DRAWINGS

These and other features, aspects, and advantages of the present invention will become better understood with reference to the following description, appended claims, and accompanying drawings where:

FIG. 2. The MAbs immunopercipitate BoNT/A Hc. BoNT/A Hc (1 mg/lane) was incubated with anti-BoNT/A Hc MAbs or anti-SEB (SEB-2Ag) MAb and the MAbs were immunoprecipitated on protein A-Sepharose. The proteins were separated on denaturing reducing gel and electroblotted onto a nitrocellulose membrane. The proteins were blotted with immunopurified rabbit polyclonal anti-BoNT/A Hc and the bound antibody was visualized using a Bio-Rad peroxidase development kit. C-fragment denotes BoNT/A Hc.

FIG. 3. Affinity mesurement of the neutralizing MAbs. Two representative of the binding analysis depicted here. Each MAbs was immobilized onto biosensor chip, after a wash-out phase, different concentrations of BoNT/A Hc were used to measure K-on and k-off.

FIG. 5. Neutralizing MAbs recognize two distinct binding sites and one overlapping epitope. MAbs 4A2-2, 4A2-4, 6E9-1, 6E9-3, 6E9-4, 6E10-4, 6E10-5, 6E10-8, and 6E10-10 recognize the same epitope. These antibodies recognize an overlapping epitope as 6C2-4. The MAb 6B2-2 recognizes a distinct epitope.

FIG. 6. Neutralizing MAbs recognize the amino acid residues within the carboxyl-terminal end of the BoNT/A Hc. The proteins were incubated with anti-BoNT/A Hc MAbs (6E9-12, 4A2-2 or 6C2-2) or anti-SEB (SEB-2Ag) MAb and the MAbs were immunoprecipitated on protein A-Sepharose. The proteins were separated on denaturing reducing gel and electroblotted onto a nitrocellulose membrane. The proteins were blotted with rabbit anti-BoNT/A Hc, peptide corresponding to N-terminal portion of BoNT/A Hc amino acid residues 915-1059 and peptide corresponding to amino acid residues within the carboxyl-terminal end of the BoNT/A Hc residues 1150-1289.

FIG. 9. Immunogenicity of the 25-mer designed peptides. Groups of ten Balb/C mice were immunized with peptide 1, peptide 2, BoNT/A Hc or control peptide by i.p. injection (40 mg per mouse for peptides and 5 mg per mouse for BoNT/A Hc). The mice were boosted with the same immunizing dose at 3, 6 and 9 weeks. Two weeks after the last immunization mice were bled and serum titres against BoNT/A Hc determined. Each filled oval represents an endpoint titer of a single animal. Data are presented as reciprocal serum dilutions resulting in the absorbance reading twice above negative control (ELISA wells contained either no BoNT/A Hc or no primary antibody). The figure shows antibody responses against peptide 1 (A), peptide 2 (B), BoNT/A Hc (C) or control peptide (D).

DETAILED DESCRIPTION

Figure 1:
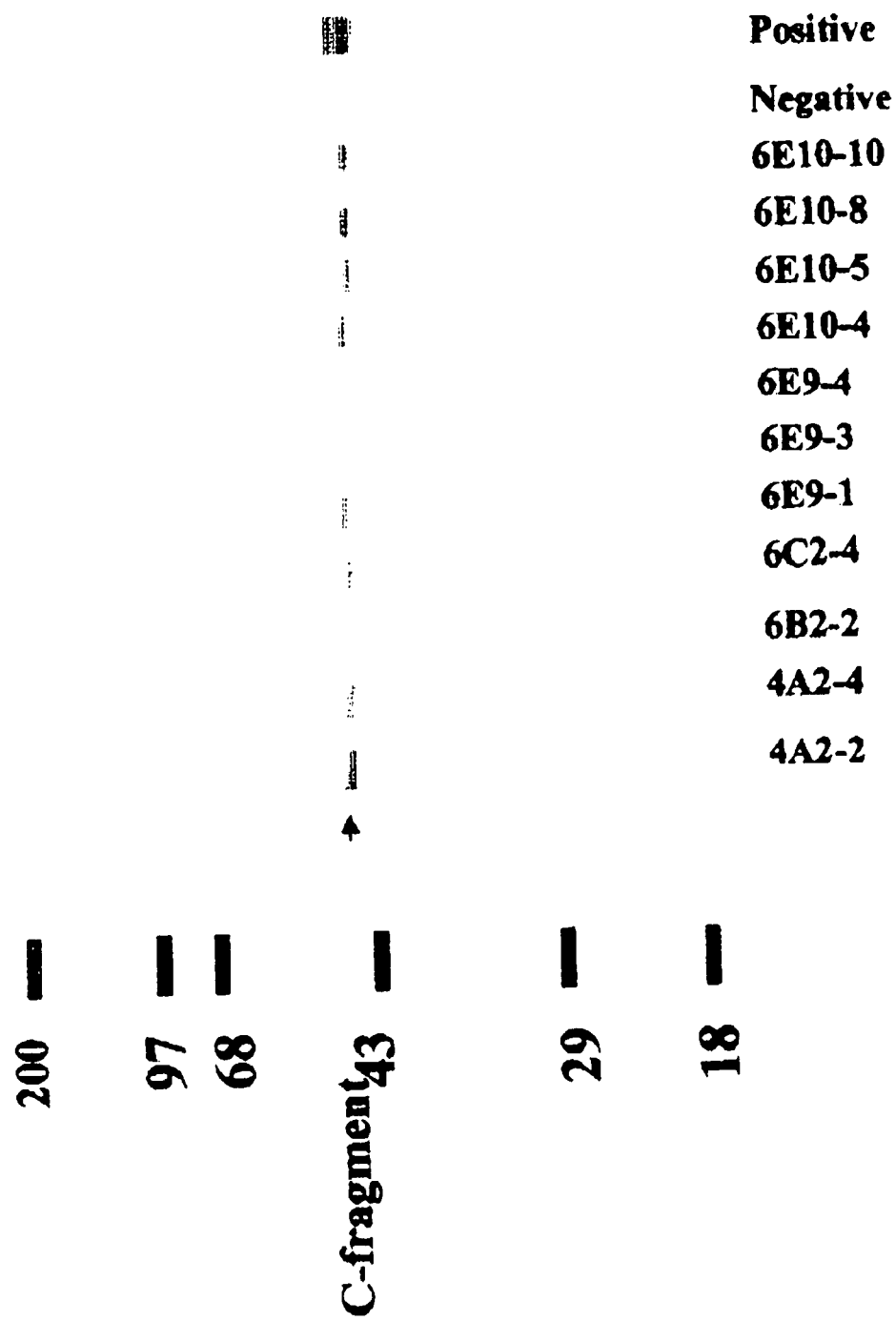
FIG. 1. Neutralizing MAbs recognize denatured BoNT/A Hc. BoNT/A Hc (1 mg/lane) was run on denaturing reducing gel and electroblotted onto a nitrocellulose membrane. The blotted paper was cut into 12 pieces and each segment was incubated with each MAb. The bound antibody was detected using color substrate. Immunopurified rabbit anti-BoNT/A Hc and SEB-2Ag were positive and negative control, respectively. C-fragment denotes BoNT/A Hc.

The present invention provides antibodies which bind to epitopes of BoNT/A and BoNT/A Hc. These antibodies can be used to purify BoNT/A from an impure solution containing BoNT/A, and to detect BoNT/A in by a sample and as a treatment for BoNT/Z intoxication. In addition, the antibodies can be used in kits for using in the methods described.

The term "antibody" is art-recognized terminology and is intended to include molecules or active fragments of molecules that bind to known antigens. Examples of active fragments of molecules that bind to known antigens include Fab and F(ab')$_2$ fragments. These active fragments can be derived from an antibody of the present invention by a number of techniques. For example, purified monoclonal antibodies can be cleaved with an enzyme, such as pepsin, and subjected to HPLC gel filtration. The appropriate fraction containing Fab fragments can then be collected and concentrated by membrane filtration and the like. For further description of general techniques for the isolation of active fragments of antibodies, see for example, Khaw, B. A. et al. *J. Nucl. Med.* 23:1011-1019 (1982). The term "antibody" also includes bispecific and chimeric antibodies.

The language "monoclonal antibody" is art-recognized terminology. The monoclonal antibodies of the present invention can be prepared using classical cloning and cell fusion techniques. The immunogen (antigen) of interest, e.g. different portions of BoNT/A or BoNT/A Hc, is typically administered (e.g. intraperitoneal injection) to wild type mice or transgenic mice which produce desired antibodies, such as human antibodies, rats, rabbits or other animal species which can produce native or human antibodies. The immunogen can be administered alone or as a fusion protein to induce an immune response. Fusion proteins comprise the peptide against which an immune response is desired coupled to carrier proteins, such as β-galactosidase, glutathione S-transferase, keyhole limpet hemocyanin (KLH), and bovine serum albumin, to name a few. In these cases, the peptides serve as haptens with the carrier proteins. After the animal is boosted, for example, three or four times, the spleen is removed and splenocytes are extracted and fused with myeloma cells using the well-known processes of Kohler and Milstein (*Nature* 256: 495-497 (1975)) and Harlow and Lane (*Antibodies: A Laboratory Manual* (Cold Spring Harbor Laboratory, New York 1988)). The resulting hybrid cells are then cloned in the conventional manner, e.g. using limiting dilution, and the resulting clones, which produce the desired monoclonal antibodies, cultured.

Examples of monoclonal antibodies raised against BoNT/A or BoNT/A Hc using this method include MAb 4A2-2, MAb 6B2-2 and MAb 6C2-4. The monoclonal antibodies MAb 4A2-2 is produced by the hybridoma deposited under American Type Culture Collection (ATCC) Accession No. PTA-971 and recognizes BoNT/A and BoNT/A Hc. MAb 6B2-2 is produced by the hybridoma deposited under American Type Culture Collection (ATCC) Accession No. PTA-969 and recognizes BoNT/A and BoNT/A Hc, and MAb 6C2-4 is produced by the hybridoma deposited under American Type Culture Collection (ATCC) Accession No. PTA-970 recognizes BoNT/A and BoNT/A Hc. Because these monoclonals recognize the carboxy terminal of the BoNT/A Hc, a region of the Hc found to form an a principal protective antigenic determinant of BoNT/A, these monoclonals may be useful for passive immunization or for reducing the symptoms of botulinum intoxication. The monoclonals and their derivatives can be administered to a subject in an amount effective to produce protection or reduce symptoms. The amount administered will depend upon the age, weight and condition of the subject as described below.

The language "polyclonal antibody" is art-recognized terminology. The immunogen used to produce the polyclonals of the present invention was the 25 kDa heavy chain of BoNT/A. The polyclonal recognizes BoNT/A. These antibodies are, therefore, useful for studying the topology of BoNT/A. In addition, these antibodies can be used to determine the orientation of BoNT/A reconstituted into artificial liposomes or virosomes. The separation of correctly-oriented from incorrectly-oriented liposomes or virosomes can be achieved using affinity chromatography. Anholt et al. *J. Biol. Chem.* 256: 4377 (1981). Because the epitopes recognized by the polyclonal antibody are solvent exposed, it is likely a useful antibody for immunoprecipitation experiments.

A common method for preparing polyclonal antibodies to an immunogen of interest, such as BoNT/A or a fragment thereof, includes injecting (e.g. intradermally, intramuscularly) an animal, such as a rabbit, with an the immunogen emulsified in Freund's complete adjuvant. This process is repeated after two weeks. Two weeks later, monthly subcutaneous booster injections can begin with the immunogen in Freund's incomplete adjuvant. The animals are bled biweekly by a marginal ear vein technique beginning six weeks after the primary immunization. The collected blood is refrigerated, allowing clots to form, and the supernatant (antiserum) retained.

The term "epitope" is art-recognized. It is generally understood by those of skill in the art to refer to the region of an antigen, such as BoNT/A, that interacts with an antibody. An epitope of a peptide or protein antigen can be formed by contiguous or noncontinguous amino acid sequences of the antigen. BoNT/A, like many large proteins, contains many epitopes. Examples of BoNT/A epitopes recognized by antibodies of the present invention include the amino acid sequences 1150-1289 of BoNT/A Hc (SEQ ID NO:1), amino acids 1157-1181 (SEQ ID NO:2), and amino acids 1230-1253 (SEQ ID NO:3). These peptides offer a convenient method for eluting BoNT/A bound to either MAb 4A2-2, 4A2-4, 6E9-3, 6E9-4, 6E10-4, 6E10-5, 6E10-8, 6E10-10, 6B2-2, and 6C2-4 on immunoaffinity columns. For example, when an antibody which recognizes the epitope for either MAb 4A2-2, MAb 6C2-4, or MAb 6B2-2, is used in an immunoaffinity column to purify BoNT/A, the peptide recognized by the antibody can be added to the immunoaffinity column to elute the BoNT/A. See below for a more detailed description of the purification of BoNT/A.

Epitope mapping studies described in this application defined three groups of MAbs, corresponding to two-distinct and one overlapping protective-epitope regions on BoNT/A Hc. One particular region of the antigen was defined by MAb 6B2-2, while 4A2-2, 4A2-4, 6E10-5, 6E10-8, 6E10-10, 6E9-3, 6E9-4, 6E9-12, and 6E10-4 MAbs bound a distinct site. The MAb 6C2-4 defined a site that overlaps with 6E10-5, 6E10-8, 6E10-10, 6E9-3, 6E9-4, 6E9-12, and 6E10-4 MAbs. However, 6C2-4 MAb bound an epitope that is distinct from 4A2-2 and 4A2-4 binding site. Thus, based on this analysis, three possible neutralizing epitopes are recognized by the MAbs of the present invention.

The epitopes to which the monoclonal antibodies bind on BoNT/A have been identified as one of the principal protective antigenic determinants of BoNT/A, suggesting that an eventual vaccine candidate may include several of these epitopes or peptides containing these antigenic determinant. The peptides were selected based on a secondary structure prediction algorithm (Rost and Sander 1994, *Protein Struct. Funct. Gen.* 20, 216-226) that located highly solvent exposed residues of BoNT/A. These highly exposed areas are postulated to be sites of interaction between antibodies and BoNT/A. We have identified two peptides described in SEQ ID NO:2 and SEQ ID NO:3 and based on binding of neutralizing MAbs to these areas, we believe that these two peptides are a part of a single protective epitope on the Hc of BoNT/A.

By further mapping of the binding site of the monoclonal antibodies described in this application other peptides useful as a vaccine or a therapeutic can be predicted. Therefore, in another aspect, this invention relates to a method for identifying protective antigenic epitopes the method comprising (i) reacting a monoclonal antibodies described in this application to different overlapping fragments encompassing the complete antigen, (ii) identifying a fragment to which the neutralizing antibody binds, (iii) narrowing the region containing sites further by reacting the monoclonal with smaller overlapping fragments encompassing the region identified in (ii), and (iv) choosing peptides to which the antibody binds as possible antigenic epitopes. The peptides can then be assayed for their ability to protect an animal from disease, or to reduce the severity of disease. Peptides defining antigenic protective epitopes can be used in a vaccine as described below and in the Examples. In addition, the peptides can be used as a therapeutic by competing with BoNT/A for its binding site on the neuron.

A vaccine or therapeutic candidate might comprise these peptide sequences and others. These might be delivered as synthetic peptides, or as fusion proteins, alone or co-administered with cytokines and/or adjuvants or carriers safe for human use, e.g. aluminum hydroxide, to increase immunogenicity. In addition, sequences such as ubiquitin can be added to increase antigen processing for more effective immune responses. Using the MAbs of the present invention, it is possible to further map peptides The present invention also pertains to hybridomas producing antibodies which bind to an epitope of BoNT/A. The term "hybridoma" is art recognized and is understood by those of ordinary skill in the art to refer to a cell produced by the fusion of an antibody-producing cell and an immortal cell, e.g. a multiple myeloma cell. This hybrid cell is capable of producing a continuous supply of antibody. See the definition of "monoclonal antibody" above and the Examples below for a more detailed description of the method of fusion. The hybridoma which produces MAb 4A2-2 is deposited under ATCC Accession Number PTA-971. The hybridoma which produces MAb 6B2-2 is deposited under ATCC Accession Number PTA-969. The hybridoma which produces MAb 6C2-4 is deposited under ATCC Accession Number PTA-970 (on Nov. 17, 1999, 10801 University Blvd., Manassas, VA 20110).

The present invention further pertains to a method for purifying BoNT/A from an impure solution containing BoNT/A. The method involves contacting the impure solution with an antibody which binds an epitope of BoNT/A, allowing the antibody to form an immunological complex, and separating the complex from the impure solution. This method can be used to clear toxic amounts of BoNT/A from any biological fluid and subjects including animals and humans.

The method of purification can further comprise separating the BoNT/A from the antibody and recovering the BoNT/A. In one embodiment, the separation is conducted by contacting the immunological complex with a saturating amount of peptide comprising the epitope recognized by the antibody of the immunological complex.

The term "purifying" is intended to include removal of unwanted constituents of an impure solution containing BoNT/A such that the concentration of BoNT/A in the solution after purification is greater that the concentration of BoNT/A in the solution prior to purification and the concentration of at least one unwanted constituent in the solution after purification is less than the concentration of the unwanted constituent in the solution prior to purification. Unwanted constituents include molecules other than BoNT/A. It should be understood that the extent of the purification of the solution can depend on the intended use of the BoNT/A. For example, the BoNT/A purified for therapeutic use will have to be more pure than BoNT/A purified for research purposes.

The language "impure solution" is intended to include a mixture of compounds which includes BoNT/A and at least one non-BoNT/A compound. For example, an impure solution can comprise a biological sample containing BoNT/A as defined below.

The language "immunological complex" is intended to include an antigen, such as BoNT/A or a fragment thereof, bound to an antibody, such as a monoclonal or polyclonal antibody, or a fragment thereof. The antigen and antibody are typically bound to one another through noncovalent interactions.

The immunological complex as well as the antigen alone can be separated from the impure solution by any separation technique known to those of ordinary skill in the art. For example, one commonly used separation method is immunoaffinity chromatography. See Harlow and Lane, *Antibodies: A Laboratory Manual* (Cold Spring Harbor Laboratory, New York 1988) 511-552. Immunoaffinity purification generally consists of three steps: preparation of an antibody-matrix, binding of an antigen to the antibody-matrix, and elution of the antigen. In the first step, either monoclonal antibodies or affinity-purified polyclonal antibodies can be covalently attached to a solid-phase matrix. An example of covalent attachment of the antibody to the solid-phase matrix is linkage of the antibody to protein A beads. See Harlow and Lane, *Antibodies: A Laboratory Manual* (Cold Spring Harbor Laboratory, New York 1988) 521-523. After the preparation of the antibody-solid phase matrix, the antigen is bound to the antibody and contaminating molecules are removed by washing. In the final step, the antigen-antibody interaction is broken by treating the immune complexes with strong elution conditions, adding a saturating amount of a small compound (e.g. the peptide comprising the epitope recognized by the antibody used in the column) that mimics the binding site, and/or treating with an agent which induces an allosteric change that releases the antigen, to release the antigen into the eluate. Optimal conditions for binding the antigen to the column, washing the column to remove contaminants, and eluting the purified antigen can be determined using conventional parameters as the starting point and testing the effect of varying the parameters. It is recognized that effective wash and elution conditions will significantly impact the degree of purification obtained. Extensive washing in the presence of stabilizers plus higher salt and differing detergents can be utilized to remove nonspecifically adsorbed proteins. Elution can then be carried out most advantageously by lowering the pH followed by immediate pH neutralization of the eluted fractions, by using the above-described specific peptide elution (Courtneige et al., 1984, *Cold Spring Harbor Conference on Cell Prolif. and Cancer* 2:123), or chaotropic agents such as potassium thiocyanate.

Although it is likely that immunoaffinity chromatography would provide a significant purification and provide protein of sufficient purity for research studies and drug screening, such an approach alone may not provide adequate protein purity to qualify BoNT/A as a clinical grade therapeutic agent. Thus, to purify the protein further, or in the case that immunoaffinity chromatography was unsuccessful, one could test a number of additional chromatographic approaches to select an optimal chromatography procedure to obtain the desired purity. For example, ligand affinity (Landry et al., 1989 *Science* 244:1469; Smigel, 1986, *J. Biol. Chem.* 261:1976), lectin (Curtis and Catterall, 1984, *Biochemistry* 23:2113), anion exchange (Hartshorne and Catterall, 1981, *Proc. Natl. Acad. Sci. USA* 78:4620) hydroxyapatite (Hartshorne and Catterall, 1984, *J. Biol. Chem.* 259:1667), and gel filtration (Borsotto et al. 1985, *J. Biol. Chem.* 260:14255) chromatographic procedures have been used in purification schemes.

The present invention still further pertains to a method for detecting BoNT/A in a sample containing BoNT/A. The method includes contacting the sample with an antibody which binds an epitope of BoNT/A, allowing the antibody to bind to BoNT/A to form an immunological complex, and detecting the formation of the immunological complex and correlating presence or absence of the immunological complex with presence or absence of BoNT/A in the sample. The sample can be biological, environmental or a food sample.

The language "detecting the formation of the immunological complex" is intended to include discovery of the presence or absence of BoNT/A in a sample. The presence or absence of BoNT/A can be detected using an immunoassay. A number of immunoassays used to detect and/or quantitate antigens are well known to those of ordinary skill in the art. See Harlow and Lane, *Antibodies: A Laboratory Manual* (Cold Spring Harbor Laboratory, New York 1988) 555-612. Such immunoassays include antibody capture assays, antigen capture assays, and two-antibody sandwich assays. These assays are commonly used by those of ordinary skill in the art. In an antibody capture assay, the antigen is attached to solid support, and labeled antibody is allowed to bind. After washing, the assay is quantitated by measuring the amount of antibody retained on the solid support. A variation of this assay is a competitive ELISA wherein the antigen is bound to the solid support and two solutions containing antibodies which bind the antigen, for example, serum from a BoNT/A vaccinee, and a monoclonal antibody of the present invention, are allowed to compete for binding of the antigen. The amount of monoclonal bound is then measured, and a determination is made whether the serum contains anti BoNT/A antibodies wherein detection of large amounts of monoclonal antibody indicates a small to no antibody against BoNT/A in the serum. This competitive ELISA can be used to predict immunity in a vaccinee following vaccination.

In an antigen capture assay, the antibody is attached to a solid support, and labeled antigen is allowed to bind. The unbound proteins are removed by washing, and the assay is quantitated by measuring the amount of antigen that is bound. In a two-antibody sandwich assay, one antibody is bound to a solid support, and the antigen is allowed to bind to this first antibody. The assay is quantitated by measuring the amount of a labeled second antibody that can bind to the antigen.

These immunoassays typically rely on labeled antigens, antibodies, or secondary reagents for detection. These proteins can be labeled with radioactive compounds, enzymes, biotin, or fluorochromes. Of these, radioactive labeling can be used for almost all types of assays and with most variations. Enzyme-conjugated labels are particularly useful when radioactivity must be avoided or when quick results are needed. Biotin-coupled reagents usually are detected with labeled streptavidin. Streptavidin binds tightly and quickly to biotin and can be labeled with radioisotopes or enzymes. Fluorochromes, although requiring expensive equipment for their use, provide a very sensitive method of detection. Antibodies useful in these assays include monoclonal antibodies, polyclonal antibodies, and affinity purified polyclonal antibodies. Those of ordinary skill in the art will know of other suitable labels which may be employed in accordance with the present invention. The binding of these labels to antibodies or fragments thereof can be accomplished using standard techniques commonly known to those of ordinary skill in the art. Typical techniques are described by Kennedy, J. H., et al., 1976 (*Clin. Chim. Acta* 70:1-31), and Schurs, A. H. W. M., et al. 1977 (*Clin. Chim Acta* 81:1-40). Coupling techniques mentioned in the latter are the glutaraldehyde method, the periodate method, the dimaleimide method, and others, all of which are incorporated by reference herein.

The language "biological sample" is intended to include biological material, e.g. cells, tissues, or biological fluid which, as it exists in nature. By "environmental sample" is meant a sample such as soil and water. Food samples include canned goods, meats, and others.

Yet another aspect of the present invention is a kit for detecting BoNT/A in a biological sample containing BoNT/A. The kit includes a container holding an antibody which binds an epitope of BoNT/A and instructions for using the antibody for the purpose of binding to BoNT/A to form an immunological complex and detecting the formation of the immunological complex such that the presence or absence of the immunological complex correlates with presence or absence of BoNT/A in the sample. Examples of containers include multiwell plates which allow simultaneous detection of BoNT/A in multiple samples.

Treatment of individuals having BoNT/A intoxication may comprise the administration of a therapeutically effective amount of BoNT/A antibodies of the present invention. The antibodies can be used as a mixture, for example in equal amounts, or individually, provided in sequence, or administered all at once. In providing a patient with antibodies, or fragments thereof, capable of binding to BoNT/A, or an antibody capable of inhibiting BoNT/A to a recipient patient, or antibodies to BoNT/A, the dosage of administered agent will vary depending upon such factors as the patient's age, weight, height, sex, general medical condition, previous medical history, etc. In general, it is desirable to provide the recipient with a dosage of antibody which is in the range of from about 1 pg/kg to 10 mg/kg (body weight of patient), although a lower or higher dosage may be administered. When providing the above-described compounds to a patient, it is preferable to administer such compounds in a dosage of antibody which is in the range of from about 1 pg/kg to 10 mg/kg (body weight of patient), although a lower or higher dosage may be administered.

The antibodies capable or inhibiting BoNT/A are intended to be provided to recipient subjects in an amount sufficient to effect a reduction in the toxicity of BoNT/A. An amount is said to be sufficient to "effect" the reduction of toxicity of BoNT/A if the dosage, route of administration, etc. of the agent are sufficient to influence such a response. Responses to antibody administration can be measured by analysis of subject's vital signs.

A composition is said to be "pharmacologically acceptable" if its administration can be tolerated by a recipient patient. Such an agent is said to be administered in a "therapeutically effective amount" if the amount administered is physiologically significant. An agent is physiologically significant if its presence results in a detectable change in the physiology of a recipient patient.

The compounds of the present invention can be formulated according to known methods to prepare pharmaceutically useful compositions, whereby these materials, or their functional derivatives, are combined in admixture with a phamaceutically acceptable carrier vehicle. Suitable vehicles and their formulation, inclusive of other human proteins, e.g., human serum albumin, are described, for example, in *Remington's Pharmaceutical Sciences* (16th ed., Osol, A. ed., Mack Easton Pa. (1980)). In order to form a pharmaceutically acceptable composition suitable for effective administration, such compositions will contain an effective amount of the above-described compounds together with a suitable amount of carrier vehicle.

Additional pharmaceutical methods may be employed to control the duration of action. Control release preparations may be achieved through the use of polymers to complex or absorb the compounds. The controlled delivery may be exercised by selecting appropriate macromolecules (for example polyesters, polyamino acids, polyvinyl, pyrrolidone, ethylenevinylacetate, metheylcellulose, carboxymethylcellulose, or protamine sulfate) and the concentration of macromolecules as well as the method of incorporation in order to control release. Another possible method to control the duration of action by controlled release preparations is to incorporate the compounds of the present invention into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, interfacial polymerization, for example, hydroxymethlcellulose or gelatin-microcapsules and poly(methylmethacylate)-microcapsules, respectively, or in colloidal drug delivery systems, for example, liposomes, albumin microspheres, microemulsions, nanoparticles, and nanocapsules or in macroemulsions. Such techniques are disclosed in *Remington's Pharmaceutical Sciences* (1980).

Administration of the antibodies disclosed herein may be carried out by any suitable means, including parenteral injection (such as intraperitoneal, subcutaneous, or intramuscular injection), in ovo injection of birds, orally, or by topical application of the antibodies (typically carried in a pharmaceutical formulation) to an airway surface. Topical application of the antibodies to an airway surface can be carried out by intranasal administration (e.g., by use of dropper, swab, or inhaler which deposits a pharmaceutical formulation intranasally). Topical application of the antibodies to an airway surface can also be carried out by inhalation administration, such as by creating respirable particles of a pharmaceutical formulation (including both solid particles and liquid particles) containing the antibodies as an aerosol suspension, and then causing the subject to inhale the respirable particles. Methods and apparatus for administering respirable particles of pharmaceutical formulations are well known, and any conventional technique can be employed. Oral administration may be in the form of an ingestable liquid or solid formulation.

The treatment may be given in a single dose schedule, or preferably a multiple dose schedule in which a primary course of treatment may be with 1-10 separate doses, followed by other doses given at subsequent time intervals required to maintain and or reinforce the response, for example, at 1-4 months for a second dose, and if needed, a subsequent dose(s) after several months. Examples of suitable treatment schedules include: (i) 0, 1 months and 6 months, (ii) 0, 7 days and 1 month, (iii) 0 and 1 month, (iv) 0 and 6 months, or other schedules sufficient to elicit the desired responses expected to reduce disease symptoms, or reduce severity of disease.

The present invention also provides kits which are useful for carrying out the present invention. the present kits comprise a first container means containing the above-described antibodies. The kit also comprises other container means containing solutions necessary or conveninet for carrying out the invention. The container means can be made of glass, plastic or foil and can be a vial, bottle, pouch, tube, bag, etc. The kit may also contain written information, such as procedures for carrying out the present invention or analytical information, such as the amount of reagent contained in the first container means. The container means may be in another container means, e.g. a box or a bag, along with the written information.

The contents of all cited references (including literature references, issued patents, published patent applications, and co-pending patent applications) cited throughout this application are hereby expressly incorporated by reference.

Other features of the invention will become apparent in the course of the following descriptions of exemplary embodiments which are given for illustration of the invention and are not intended to be limiting thereof. The following materials and method were used in the examples below.

MATERIALS AND METHODS

Antigens

BoNT/A was purchased from List Biochemicals (Campbell, Calif.), and BoNT/A HC, BoNT/B HC, BoNT/E HC were kindly provided by L. Smith (USAMRIID, Frederick, Md.). The BoNT/A HC preparation was analyzed by SDS-PAGE (12%) and stained with Coomassie Brilliant Blue R 250 (Sigma Chemical Comp. St Louis, Mo.) in methanol (10% v/v) acidic acid (10% v/v) and found to be at least 95% pure.

The pentavalent toxoid, composed of BoNT serotypes A-E, was obtained from the Bureau of Laboratories, Michigan State Department of Public Health (Lansing, Mich.). The five recombinant, overlapping fragments encompassing H of BoNT/A, were purified and generously provided by M. Dertzbaugh (USAMRIID) who previously reported their expression in *Escherichia coli* (Dertzbaugh and West, 1996, Vaccine 14, 1538-1544). The molecular masses of these proteins ranged from 18- to 23-kDa. Three 25-mer peptides (SEQ ID NO:2 and SEQ ID NO:3), whose sequences correspond to regions within BoNT/A, were synthesized, purified, and sequenced by Quality Controlled Biochemicals, Inc. (Hopkinton, Mass.). An additional cysteine residue was added to some of the peptides for biotinylation procedures.

Experimental Animals

Pathogen-free Balb/C(H-2d) mice, 10- to 12-weeks old, were obtained from Harlan Sprague-Dawley, Inc. (Frederick Cancer Research and Development Center, Frederick, Md.). Mice were maintained under pathogen-free conditions and fed laboratory chow and water ad libitum.

Immunization and Hybridoma Production

Mice were immunized intraperitoneally (i.p.) four times at 4-week intervals with 2 µg of BoNT/A Hc in 100 µl phosphate-buffered saline (PBS; 50 mM sodium phosphate, 140 mM sodium chloride, pH 7.4). Mice were bled 2 weeks after the last vaccination and titers against BoNT/A and BoNT/A HC were determined. Two mice with the highest titers were selected for hybridoma production. One month after the last vaccination, these mice were given (ip) 0.1 µg of the antigen and 5 days later, spleens were removed from immunized mice. Splenic mononuclear cells were collected and fused at a ratio of 3 to 1 with myeloma cells in medium containing polyethylene glycol. After the HAT selection, the supernatants of the hybridoma cells were tested by ELISA for the presence of antibodies to the BoNT/A and BoNT/A Hc. Positive hybridoma supernatants were tested for their ability to neutralize BoNT/A, as described below. Limiting dilution was used to clone the hybrids that produced neutralizing antibodies, and 33 hybridoma clones secreting MAbs against BoNT/A Hc were isolated.

Screening of Hybridoma Supernatants, Antibody Purification, Quantification of MAbs Either intact BoNT/A or BoNT/A Hc in 100 µl of PBS was coated onto microtiter plates at 0.2 µg/well (37° C., 2 h). The wells were blocked with 250 µl of 0.2% casein in PBS (37° C., 2 h) and then washed four times with wash buffer (PBS containing 0.2% Tween 20, pH 7.4) before incubation for 1 h at 37° C. with hybridoma supernatants. The cell free hybridoma supernatants were added undiluted or diluted 1:10 in PBS containing 0.02% casein. After washing, bound antibody was detected with horseradish peroxidase (HRP)-labelled goat anti-mouse IgG (Sigma) (37° C., 1 h), with 0 phenylenediamine as the chromogen. Mean of duplicates OD (absorbance at 490 nm) of each sample was obtained and scored as positive if the OD was two times above the negative control wells were. For negative controls, antigen or serum was omitted from the wells Purification of MAbs was accomplished using Protein G conjugated to Sepharose (Pharmacia Biotech, Uppsala, Sweden) according to manufacturer's instructions.

For quantitation, dilutions of purified MAbs were added to ELISA wells coated with anti-mouse IgG (Sigma chemical Comp., St. Louis, Mo.). After 1 h incubation at 37° C., the captured MAbs were detected using HRP conjugated goat anti-mouse IgG (Cappel/Organon Teknika Corp., West Chester, Pa.) (37° C., 1 h) and O-phenylenediamine as the chromogen. The microtiter-wells were read at 490 nm wells with optical density values greater than two times of the control wells were scored as positive. Standard curves were prepared by plotting the mean of duplicate densitometric readings for each dilution of IgG standard. The resulting values were fitted to a straight line by linear regression. Concentrations of MAbs were determined by comparing mean values of various dilutions of the antibody to the standard curve.

Isotype and Subclass Identification

MAb isotype and subclass was determined by standard direct ELISA according to manufacturer's instructions (Sigma Chemical Comp.).

Western-immunoblotting and Immunoprecipitation

BoNT/A Hc (1 µg/lane) was separated by SDS-PAGE and transferred to nitrocellulose membranes (Bio-Rad Lab. Inc., Melville, N.Y.) by electroblotting. Nonspecific sites on the membranes were blocked (12 h 4° C.) with 0.2% casein in a buffer consisting of 50 mM sodium phosphate, 140 mM sodium chloride, pH 7.4 (PBS). The membranes were then incubated (overnight, room temp, shaking) with 2 µg/mL of affinity purified anti-BoNT MAb in PBS containing 0.02% casein. After the membranes were thoroughly washed, HRP-conjugated goat anti-mouse IgG (Cappel/Organon Teknika Corp. West Chester, Pa.) was added (1:5,000) and the membranes were incubated for 1 h (37° C.) with shaking. Unbound antibody was removed by washing with PBS and bound antibody was visualized using a Bio-Rad peroxidase development kit.

For immunoprecipitation experiments, nonspecific sites on recombinant protein A-Sepharose (Repligen Corp., Cambridge, Mass.) were blocked using 0.2% casein in 10 mM Tris-HCl, pH 7.4 with 150 mM NaCl (TBS) for 2 h at 37° C. Unreacted supernatants were collected by centrifugation and then the precleared protein A-Sepharose (100 µof 50% suspension) were incubated (37° C., 2 h, with mixing) with 2 µg of the MAb in 200 µl of TBS. Immunoadsorbents were collected by centrifugation, washed four times with the same buffer containing 0.02% casein. Bound proteins were eluted by boiling the samples (95° C., 10 min) in SDS-PAGE buffer containing 5 mM dithiothreitol. The samples were electrophoresed through 12% polyacrylamide gels and analyzed by immunoblotting, as described above.

Neutralization Assays

Serial dilutions of MAbs were incubated with various lethal doses of BoNT/A for 1 h at room temperature. The toxin and antibody mixture was administered i.p at a dose of 0.2 ml per mouse. Five days after challenge, the mice were scored for survivors. In initial neutralization assays, mice were observed for up to 20 days.

Binding Kinetics Using Surface Plasmon Resonance

The affinities of MAbs produced to BoNT/A HC were determined with an optical biosensor using real-time surface plasmon resonance technology (SPR; BIAcore 1000 with upgrade; Biosensor, Pharmacia, San Diego, Calif.). Affinity-purified antibody to mouse IgG Fc and biosensor CM-5 chips were purchased from BIAcore AB, (Uppsala, Sweden). The anti-Fc antibody was coupled to the chip with N-hydroxysuccinimide and N-ethyl-N' (dimethylaminopropyl) carbodiimide, according to the manufacturer's protocol. Each purified BoNT/A HC MAb was captured by the chip immobilized, anti-IgG Fc antibody. Kinetic analyses were carried out at a flow rate of 25 µl/min with 5-200 nM BoNT/A HC in HEPES buffered saline. Values for apparent equilibrium dissociation constant (KD) were calculated from the ratio of association (kon) and dissociation (koff) rate constants obtained with the BIAevaluation 2.1 software package supplied by the vendor. Biosensor chips with bound anti-IgG Fc antibody were regenerated by removing the bound MAbs with two 30-sec pulses of 10 mM glycine (pH 1.8).

Epitope Mapping Using Biosensor Technology

Epitope mapping of the MAbs was carried out by surface plasmon resonance at a flow rate 5 µl/min. Affinity-purified antibody to mouse IgG Fc was immobilized onto the chip, purified BoNT/A HC MAb was captured by the antibody, and then nonspecific sites were blocked by passing a saturating concentration of an unrelated antibody over the matrix surface. BoNT/A HC (200 nM) in HEPES buffered saline was passed over the antibodies at a flow rate of 5 µl/min. Finally, the second (competing) MAb was injected, and its binding determined. The biosensor chip was regenerated as above, and the process was repeated to test the ability of all MAbs to bind as second MAb using each MAb as first MoAb. Thus, all antibody pairs were tested in both directions.

Peptide Immunizations

Ten- to 12-week old mice were immunized (i.p.) with various amounts of peptides in 100 µl of RIBI adjuvant (RIBI Immunochem Research, Inc. Hamilton, Mont.), 2-5 µg of BoNT/A/B/E-Hc, or 0.2 ml of pentavalent BoNT toxoid vaccine. The mice were boosted intraperitoneally (i.p.) at 3 and 6 weeks. In some experiments, peptide-immunized mice received a third boost at 9 weeks. Serum samples were collected from tail veins 2 weeks after the last immunization. Mice were challenged 2-3 weeks after the last injection with intact BoNT/A. Uninjected or adjuvant-injected mice served as challenge controls.

Antibody Assay

Microtiter plates were coated with 0.2 µg/well of intact BoNT/A, Hc of BoNT/A, or peptide (1 µg/well) in 100 µl of PBS (37° C., 2 h). After antigen coating, the wells were blocked with 250 µl of 0.2% casein in PBS (37° C., 2 h) and then washed four times with PBS containing 0.2% Tween 20. Immune or nonimmune mouse sera were diluted in PBS containing 0.02% casein; 100 µl of each dilution was added to duplicate wells. After each well was washed four times, bound antibody was detected with horseradish peroxidase (HRP)-labelled goat anti-mouse IgG (Sigma) (37° C., 1 h), with 0-phenylenediamine as the chromogen. The mean of duplicate OD (absorbance at 490 nm) of each treatment group was obtained and these data were compared on the basis of the inverse of the highest serum dilution that produced an OD reading two times greater than the value from the negative control wells. For negative controls, antigen or serum was omitted from the wells.

Analysis of MAb Binding to the Designed Peptides

The procedure for peptide-specific ELISA was the same as that described above except that microtiter wells were coated with 1 μg of goat affinity-purified antibody produced to mouse IgG Fc (Organon Teknika Corp. West Chester, Pa.). Non-specific sites were blocked with 250 μl of casein 0.2% in PBS (37° C., 2 h) and then washed four times with PBS containing 0.2% Tween 20. Every MAb was incubated with each biotinylated-peptide (37° C., 2 h). The mixture was then added to the anti-IgG Fc-coated wells and incubated at 37° C. for 2 h. Unbound peptide was washed out of the wells and the bound peptide-MAb complexes were detected by streptavidin-HRP (SA-HRP; Immunotech, Inc. Westbrook, Me.).

EXAMPLE 1

Generation of Neutralizing MAbs to BoNT/A

We hypothesized that neutralizing antibodies against BoNT/A might be best generated if one immunizes animals with BoNT/A Hc, the protective, non-toxic receptor-binding domain of BoNT/A. To generate such MAbs, spleen cells from the highly seropositive mice were fused with myeloma cells. To avoid isolation of antibodies that show little to no reactivity against the whole toxin, all of the fusion product supernatants were screened by a direct ELISA on 96-well plates containing whole BoNT/A or BoNT/A Hc. This vaccination approach produced 660 hybridoma fusions that recognized BoNT/A HC and from these hybridoma fusions 488 recognized the native toxin in an ELISA-based assay. To increase the possibilities of finding neutralizing antibodies, we elected to examine protective ability of all 488 fusion-products that recognized the toxin in an in vivo mouse lethality model prior to cloning and subsequent subclonning of the hybrids. The cells corresponding to the positive wells were transferred to 6-well plates and cultured for 7-10 days. The culture supernatants were tested for their ability to protect mice against 10 LD50 of BoNT/A. We obtained 33 hybrids that produced neutralizing antibody and these fusion-products were cloned. Candidate hybridomas were subjected to a second round of expansion and screening, and were subcloned. Eleven hybridomas were cloned and antibodies were immunopurified using protein G columns. The MAbs were named: 4A2-2, 4A2-4, 6B2-2, 6C2-4, 6E10-5, 6E10-8, 6E10–10, 6E9-3, 6E9-4, 6E9-12, and 6E10-4. When MAbs were tested against 20 LD50 of BoNT/A, mice were protected fully (3/3 mice survived). The specificity of the MAbs was analyzed by ELISA. The MAbs only recognized BoNT/A HC and showed no binding to other BoNTs HC and the antibodies did not offer any protection against other BoNTs (Table 1). These results indicate that immunization with the protective fragment of BoNT/A elicits production of substantial numbers of neutralizing MAbs.

TABLE 1

| BoNT/A neutralizing MAbs do not protect against hetrologous BoNTs | | | |
|---|---|---|---|
| MAb | BoNT serotype | LD50 | Live/death |
| 4A2-2 | A | 5 | 5/0 |
| 4A2-2 | B | 5 | 0/5 |
| 4A2-2 | E | 5 | 0/5 |
| 6B2-2 | A | 5 | 5/0 |
| 6B2-2 | B | 5 | 0/5 |
| 6B2-2 | E | 5 | 0/5 |

TABLE 1-continued

| BoNT/A neutralizing MAbs do not protect against hetrologous BoNTs | | | |
|---|---|---|---|
| MAb | BoNT serotype | LD50 | Live/death |
| 6C2-4 | A | 5 | 5/0 |
| 6C2-4 | B | 5 | 0/5 |
| 6C2-4 | E | 5 | 0/5 |

The antibody was premixed and incubated for 1 hr prior to administration to mice.

EXAMPLE 2

Chracterization of the Neutralizing MAbs

To begin to explore the binding characteristics of the antibodies, we examined in a variety of conditions the interaction of the neutralizing MAbs with the intact BoNT/A and BoNT/A HC including Western immunoblot, and immunoprecipitation. As can be seen in FIG. 1a, the MAbs recognized a 50 kD protein corresponding to BoNT/A HC. Next we examined the subunit specificity and epitope of the MAbs were analyzed by Western immunoblotting. Purified BoNT/A was boiled in 2-mercaptoethanol containing SDS solution, gel electrophoresed, and then Western blotted using the MAbs. As can be seen in FIG. 1b, BoNT/A degrades into two bands one at approximately 50 kD and the other one at about 100 kD which these bands correspond to the light chain and the H chain, respectively. As expected, the MAbs only recognized the H chain. We were also interested to evaluate the abilities of the antibodies to detect BONT/A HC under more physiological conditions. To test this, we studied immunoprecipitating soluble BoNT/A HC using the neutralizing antibodies and then the bound immune complexes was detected following immunoblotting with rabbit anti-BoNT/A Hc antibody (FIG. 2). All MAbs immunoprecipitated the antigen with the same intensity.

To characterize the kinetic interactions between the neutralizing MAbs BoNT/A Hc, we elected to use the SPR (surface plamon resonance) biosensor technology. Each antibody was captured on a biosensor chip, various concentrations of BoNT/A Hc were passed through the flow cell and the binding kinetics recorded. Equilibrium dissociation constants and kinetic on-off rates were measured from the ascending rate of BIAcore signal during binding and descending rate during wash-off interval. An example of the SPR studies using MAb 6B2-2 is seen in FIG. 3, this figure shows that 6B2-2 possessed an unusually long Koff rate. We used SPR and calculated the apparent dissociation constants (KD) of each MAb for BoNT/A HC. Table 2 shows that the majority of the MAbs had similar association rate and their overall values for KD were in the range of $10^{-10}$ M. The KD for one of the MAb, 6B2-2, was extremely lower ($<5\times10^{-11}$ M) but was difficult to resolve accurately due to its substantially slow rate of dissociation, as compared with the other MAbs. Because the overall affinities were similar for the MAbs examined, we suggest that differences in the binding affinities played only a minor role in the neutralizing ability of the MAbs.

TABLE 2

Kinetic constant of BoNT/A MAbs for BoNT/A Hc

|  | k-off | k-on | KD (nM) |
|---|---|---|---|
| 4A2-2 | $3.5 \times 10^{-4}$ | $6.9 \times 10^5$ | 0.51 |
| 4A2-4 | $4.2 \times 10^{-4}$ | $7.8 \times 10^5$ | 0.54 |
| 6B2-2 | $<0.2 \times 10^{-4}$ | $3.1 \times 10^5$ | $<0.06$ |
| 6C2-4 | $1.9 \times 10^{-4}$ | $17.0 \times 10^5$ | 0.11 |
| 6E9-1 | $2.5 \times 10^{-4}$ | $11.0 \times 10^5$ | 0.22 |
| 6E9-3 | $2.8 \times 10^{-4}$ | $11.0 \times 10^5$ | 0.25 |
| 6E9-4 | $6.7 \times 10^{-4}$ | $7.8 \times 10^5$ | 0.86 |
| 6E10-4 | $5.3 \times 10^{-4}$ | $11.0 \times 10^5$ | 0.48 |
| 6E10-5 | $3.9 \times 10^{-4}$ | $4.8 \times 10^5$ | 0.81 |
| 6E10-8 | $2.1 \times 10^{-4}$ | $4.9 \times 10^5$ | 0.42 |
| 6E10-10 | $3.1 \times 10^{-4}$ | $14.0 \times 10^5$ | 0.22 |

Kinetic constant was measured with SPR.

Figure 4:
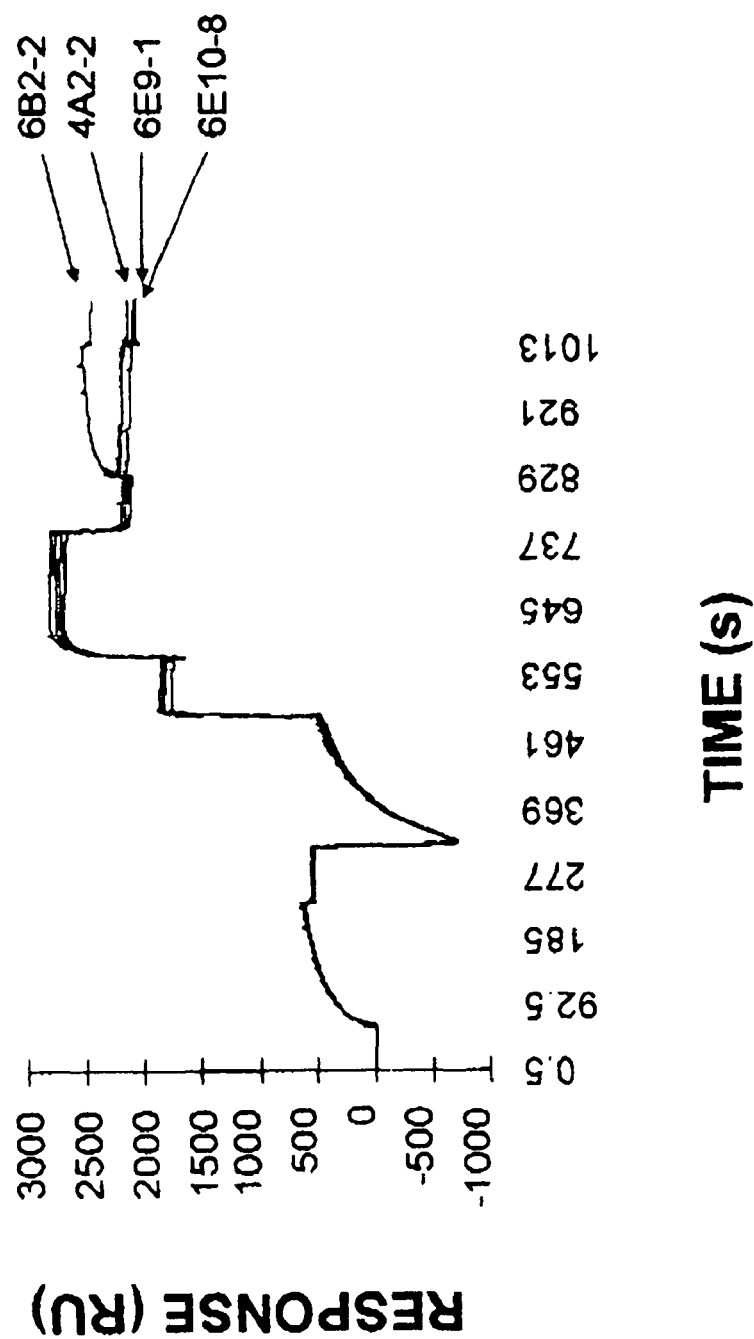
FIG. 4. The MAb 6B2-2 binds to a distinct epitope on BoNT/A. Epitope mapping of the MAbs was carried out by SPR, Affinity-purified antibody to mouse IgG Fc was immobilized onto the chip. Purified-BoNT/A HC MAb was captured by the antibody, and then nonspecific sites were blocked by passing a saturating concentration of an unrelated antibody over the matrix surface. BoNT/A HC (200 nM) in HEPES buffered saline was passed over the antibodies at a flow rate of 5 µl/min. Finally, the second (competing) MAb was injected, and its binding determined. The biosensor chip was regenerated and the process was repeated to test the ability of all MAbs to bind as second MAb using each MAb as first MoAb.

Next, we used SPR to characterize the binding sites of the Abs. In these studies, we used anti-mouse antibody to capture the BoNT/A Hc MAb, followed by BoNT/A Hc. A second competing MAb, was injected, and its was binding determined. This experiment was repeated to examine the ability of all MAbs to bind as second MAb using each MAb as first MAb. This type of approach tested all pairs of antibodies in both directions. As seen in an example in FIG. 4, when 4A2-2 MAb was immobilized onto the sensor chip and the same antibody or other heterologous antibody, 6B2-2, 6E9-1, and 6E10-8, respectively, were injected sequentially, only competing MAb 6B2-2 bound. All combination of antibodies was tested likewise and the data obtained are summarized in FIG. 5. The epitope mapping studies defined three groups of MAbs, corresponding to two-distict and one overlapping protective-epitope regions on BoNT/A Hc. One particular region of the antigen was defeined by MAb 6B2-2, while 4A2-2, 4A2-4, 6E10-5, 6E10-8, 6E10–10, 6E9-3, 6E9-4, 6E9-12, and 6E10-4 MAbs bound a distinct site. The MAb 6C2-4 defined a site that overlaps with 6E10-5, 6E10-8, 6E10–10, 6E9-3, 6E9 4, 6E9-12, and 6E10-4 MoAbs. However, 6C2-4 MAb bound an epitope that is distinct from 4A2-2 and 4A2-4 MoAb binding site. Thus, based on this analysis, we are proposing that there are at leat two, possibly three, neutralizing epitopes on BoNT/A Hc.

EXAMPLE 3

Immunization with pentavalent toxoid (composed of BoNT serotypes A-E) or $H_c$ of BoNT/A produced high antibody titers against BoNT/A and protected mice against 10, 100, and 1000 $LD_{50}$ of BoNT/A (Table 3). However, when mice were vaccinated with $H_c$ of BoNT serotype B or E, little to no antibody against BoNT/A was detected. These mice were not protected when challenged with 10 $LD_{50}$ BoNT/A. This experiment suggests there was little to no cross-protection among these serotypes, and that the majority of protective epitopes of BoNT/A was located within Hc (Dertzbaugh and West, 1996, supra; Clayton et al., 1995, *Infect. Immun.* 63, 2738-2742).

TABLE 3

Immunization with BoNT/A Hc confers protection

| Immunization[a] | Titer[b] | Challenge[c] | Live/Dead[d](LD50) |
|---|---|---|---|
| Toxoid | $10^5$ | 10 | 10/0 |
| Toxoid | $10^5$ | 100 | 10/0 |
| Toxoid | $10^5$ | 1,000 | 10/0 |
| BoNT/A Hc | $10^5$ | 10 | 10/0 |
| BoNT/A Hc | $10^5$ | 100 | 10/0 |
| BoNT/A Hc | $10^5$ | 1,000 | 10/0 |
| BoNT/B Hc | $<10^2$ | 10 | 1/9 |
| BoNT/E Hc | $<10^2$ | 10 | 0/10 |

[a] Mice were vaccinated i.p. and boosted at 3 and 6 weeks.
[b] Two weeks after the last immunization, mice were bled and serum titers against BoNT/A determined. Data are presented as reciprocal serum dilution resulting in OD reading twice above negative controls(ELISA wells containing either no BoNT/A or no primary antibody).
[c] Mice were challenged with BoNT/A 3 weeks after the final boost.
[d] Lethality was recorded 7 days after the challenge dose.

To identify the sites that contain the neutralizing epitopes, protective MAbs to the Hc of BoNT/A were produced in mice.

Figure 6:
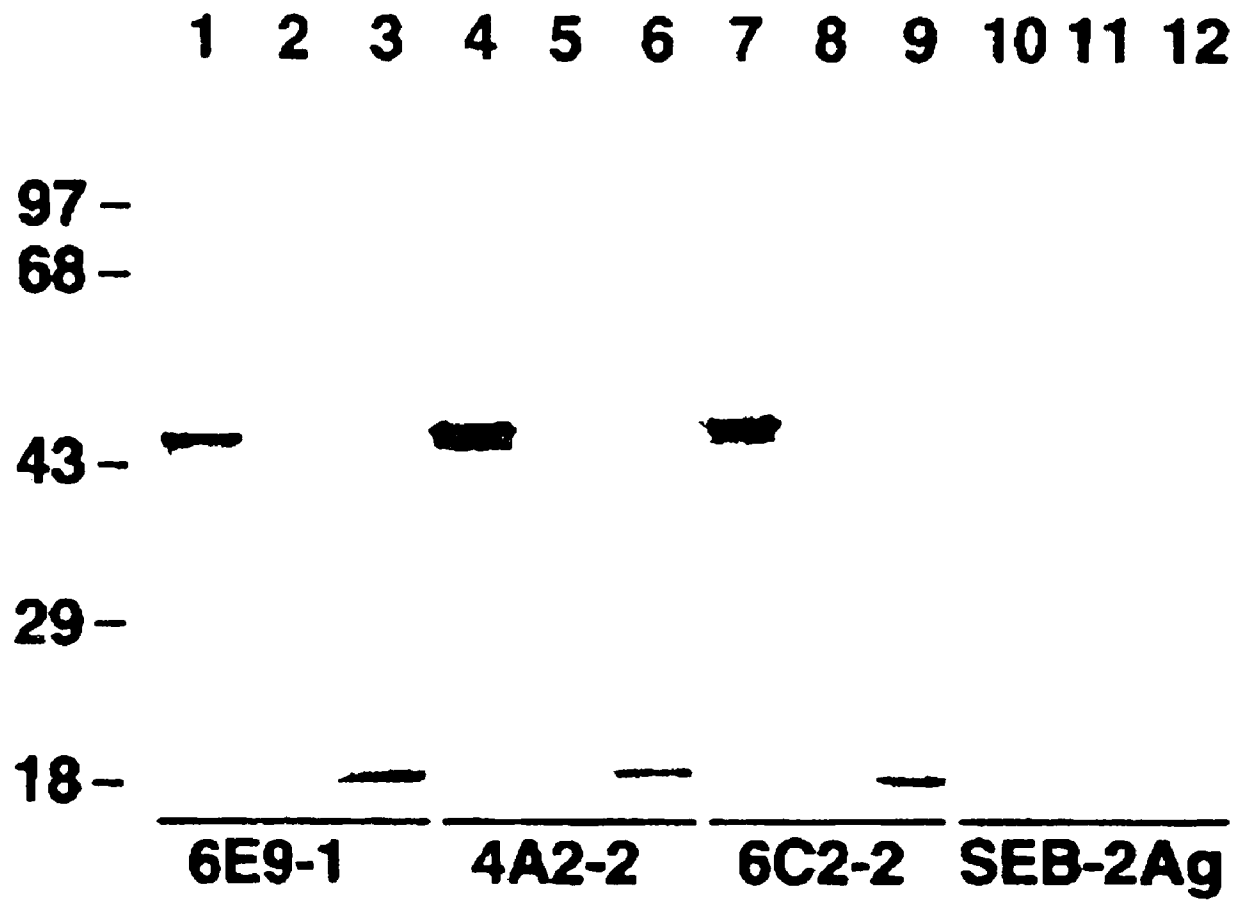

To characterize the region of BoNT/A $H_c$ that these MAbs recognized, the MAbs were reacted separately to each of five recombinant overlapping fragments encompassing $H_c$ of BoNT/A-Hc (Dertzbaugh and West, 1996, supra). As expected, MAbs were able to immunoprecipitate $H_c$ of BoNT/A (~50 kDa) (FIG. 6). The MAbs, 6E9-12, 4A2-2, and 6C2-2, immunoprecipitated the fragment corresponding to residues 1150-1289. However, none of the MAbs recognized the truncated fragment corresponding to the N-terminal portion of BoNT/A $H_c$ amino acid residues 915-1059. Although the other fragments were not recognized, or were only recognized weakly, by the MAbs, they were recognized by polyclonal antibodies produced to BoNT/A $H_c$, which suggested that they may contain other B-cell epitopes (data not shown). Control MAb (SEB-2Ag) produced to a bacterial superantigen (Ulrich et al., 1995, *Trends Microbiol.* 3, 463-468), staphylococcal enterotoxin B (SEB), did not immunoprecipitate any of the fragments. Of the fragments derived from BoNT/A $H_c$, only immunization with the 1150-1289 peptide, which contained the residues within the carboxyl-terminal end of the BoNT/A $H_c$, protected mice from BoNT/A challenge (Dertzbaugh and West, 1996, supra). Together, these data strongly suggest that the majority of PPDs of BoNT/A reside within the carboxyl-terminal end of the molecule.

To localize further the sites of PPDs, three 25-mers were synthesized (Table 4). These peptides were constructed based on a secondary structure prediction algorithm that located highly solvent-exposed residues of BoNT/A Hc (Lebeda and Olson, 1994, *Prot. Struct. Func. Gen.* 20, 230-300; Sander et al., 1991, *Proteins* 9, 56-68; Rost and Sander, 1994, *Prot. Struct. Func. Gen.* 19, 55-72; Lebeda and Olson, 1995, *Toxicon* 33, 559-567; Lebeda and Olson, 1997, *J. Prot. Chem.* 16, 607-618). The predictions used for this study are considered to be highly accurate based on the recently determined X-ray crystal structure of TeTN Hc (Lebeda and Olson, 1998, *J. Prot. Chem.; Umland et al.*, 1997, supra). As a control, a 25-mer peptide was prepared by using a sequence from N-terminal portion of the H-chain. This portion was also predicted to be solvent-exposed. We selected peptides 1 (SEQ ID NO:2) and 2 (SEQ ID NO:3) because segments of these peptides were predicted to represent the most highly exposed surfaces of BoNT/A Hc (Lebeda and Olson, 1994, supra).

Figure 7:
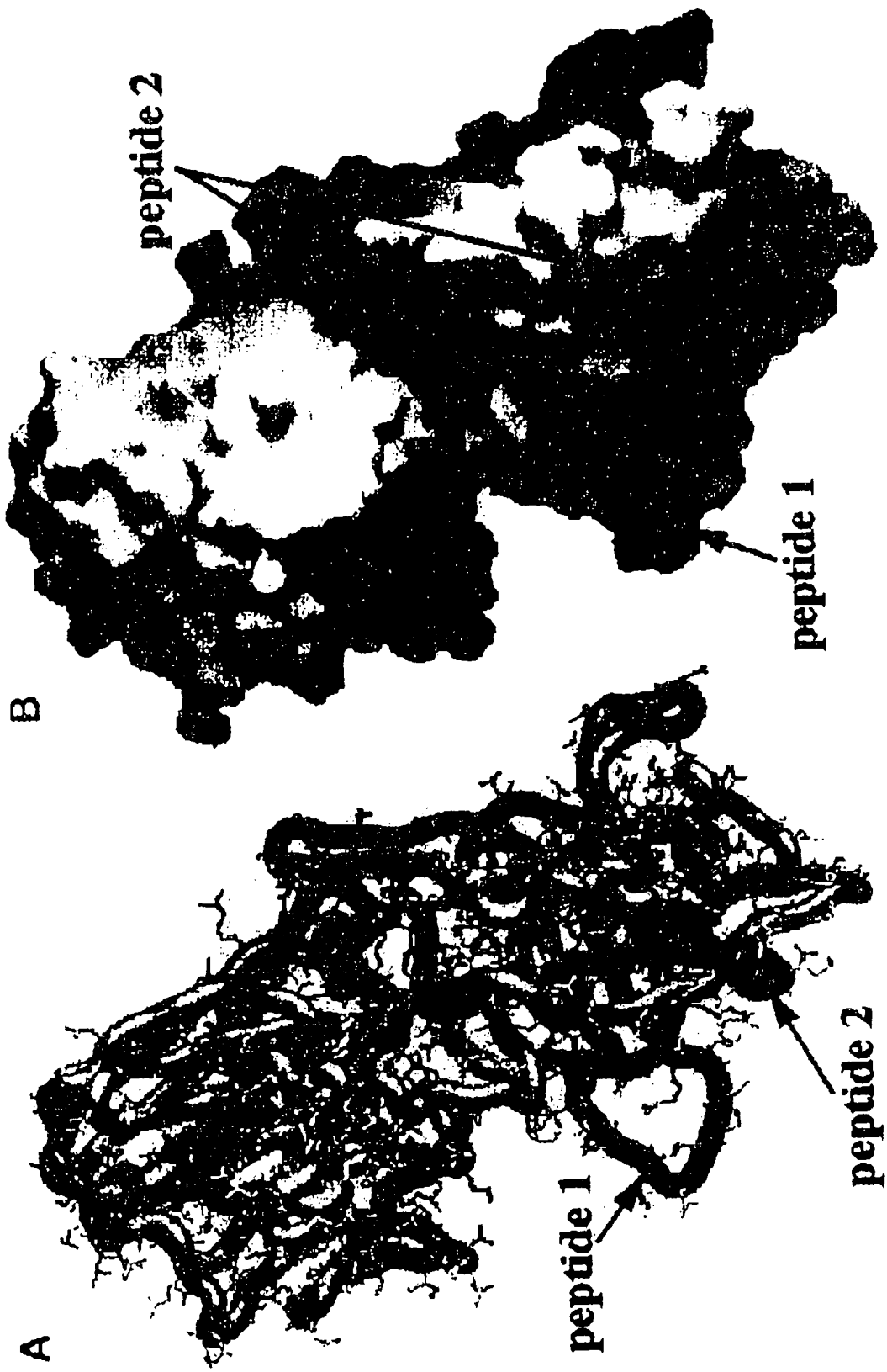
FIG. 7. Location of amino-acid residues corresponding to the designed peptides. The figure represents the X-ray crystallographic structure of TeNT-HC on which the positions of amino acids corresponding to peptide 1 and peptide 2 are distinguished. Panel (A) shows the alpha-carbon backbone tracing or, panel (B) depicts the molecular surface of TeNT-HC.

The locations of the two peptides, using the tertiary structure of TeNT Hc (Umland et al., 1997, supra), are depicted in FIG. 7.

TABLE 4

Sequence of synthetic 25-mer peptides

| Peptides | BoNT/A Amino acid | Sequence[a] | SEQ ID NO: |
|---|---|---|---|
| Control | 449-473 | ALNDLCIKVNNWDLFFSPSEDNFTN | 4 |
| One | 1157-1181 | GTKFIIKKYASGNKDNIVRNNDRVY | 2 |
| Two | 1230-1253 | GITNKCKMNLQDNNGNDIGFIGFHQ | 3 |

[a]In some experiments, an additional cysteine residue was added to N-terminus for biotinylation procedures.

Figure 8:
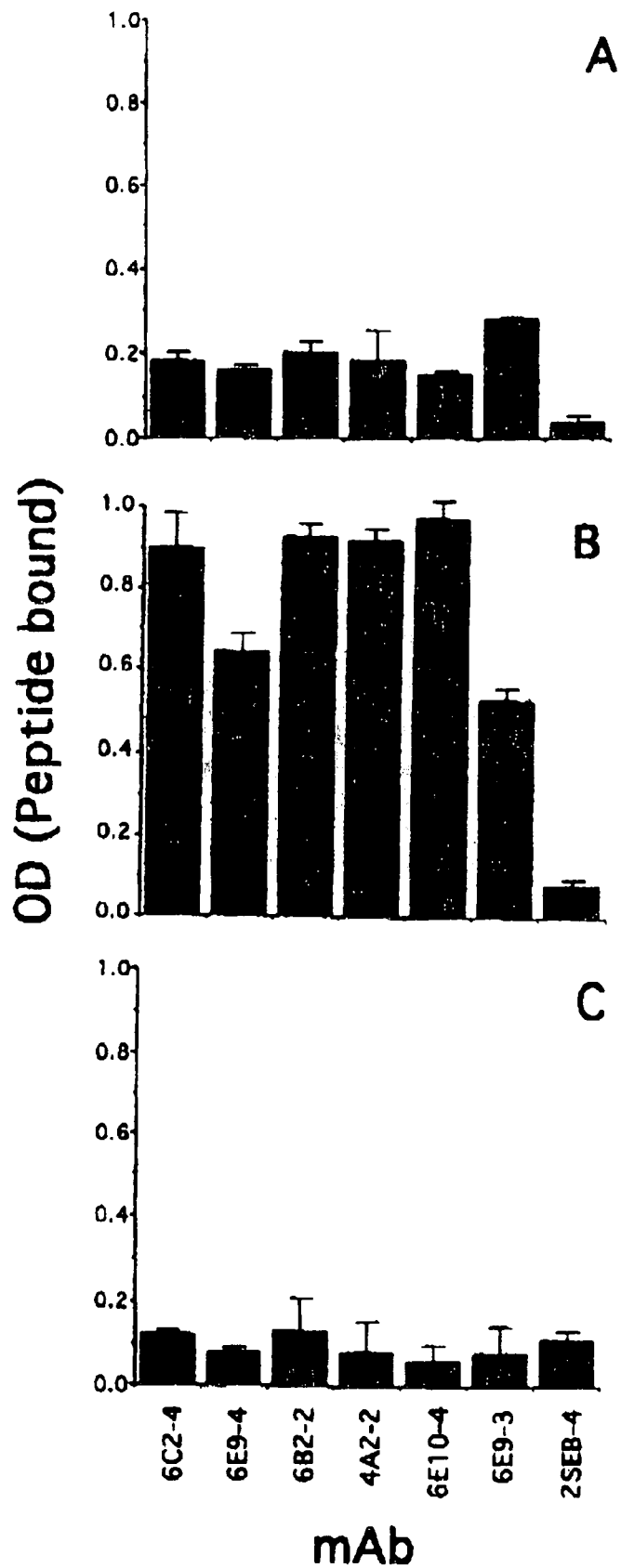
FIG. 8. Binding of protective MAbs to designed peptides. The ability of MAbs to recognize peptide 1 (A), peptide 2 (B) or control peptide (C) are depicted. The biotinylated-peptides were incubated with MAbs and then transferred to anti-IgG Fc coated ELISA wells. The bound biotinylated-peptide in complex with MAb was depicted using streptavidin.

Because recognition of a peptide by neutralizing MAbs is a prerequisite for the presence of PPADs, we examined binding of the MAbs to engineered synthetic peptides. The antibodies were incubated with biotin-labelled peptides, and then the complexes were captured on the wells of ELISA plates by anti-IgG Fc antibodies. Bound peptides in complex with the neutralizing MAb were detected using streptavidin. The neutralizing MAbs recognized both peptides that were predicted to be highly exposed (FIG. 8a,b), while the control peptide was not recognized (FIG. 8c). Although both peptides were similarly highly exposed, peptide 2 was better recognized than peptide 1 by the MAbs. We failed to detect any interaction between the peptides and anti-SEB MAb (SEB-2Ag) (FIG. 8). Because all of the MAbs examined recognized both $H_c$-peptides, it is likely that these spatially proximal peptides correspond to a single neutralizing epitope on the Hc of BoNT/A.

Figure 9:
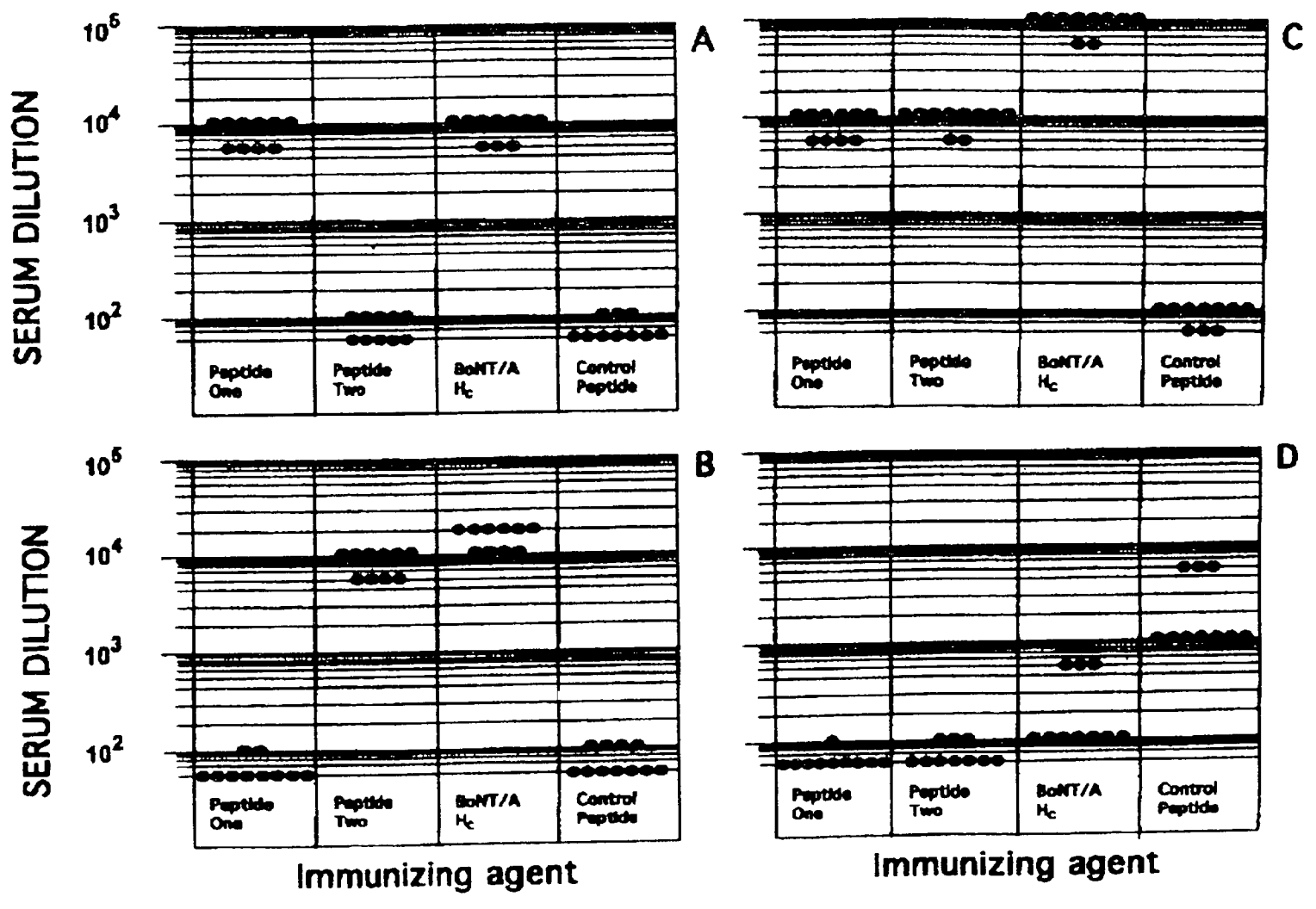

Because these peptides were recognized by MAbs, this suggested that the peptides may contain some or all of the PPADs within BoNT/A $H_c$, and may have vaccine efficacy. First, the immunogenicity of the peptides in mice was examined (FIG. 9). In contrast to BoNT/A $H_c$, the highest antibody responses to the peptides were elicited only after the fourth dose (FIG. 9). Both peptides 1 and 2 induced a good antibody response when the peptide or BoNT/A $H_c$ was used as immunogen in an ELISA. As we expected, peptides elicited little cross-reactive antibody responses to other peptides. Mice immunized with peptide 1 did not develop an antibody response against peptide 2. The same scenario was observed when mice were immunized with peptide 2 and antibody titers were measured against peptide 1. Immunization with BoNT/A $H_c$ yielded high titer antibodies that recognized both peptides; however, there were overall higher titers against peptide 2. These data suggest that antibodies against these peptides may be naturally produced when mice are immunized with $H_c$, and that peptide 2, not peptide 1, is the immunodominant antigen. Experiments are in progress to better address this observation. In support of this notion, sera obtained from human volunteers immunized with BoNT pentavalent toxoid also recognized synthetic peptides corresponding to these two regions (Atassi et al., 1996, *J. Prot. Chem.* 15, 691-700). Other experiments suggested that these two peptides may also contain T-cell epitopes (data not shown). Mice injected with low doses of BoNT/A $H_c$ produced high titers, that were much higher than those elicited by the peptides. We observed the high titers after the third immunization. Endpoint antibody titers against $H_c$ for mice injected with BoNT/A $H_c$ are shown in FIG. 9c. Control peptide produced little to no antibody to either peptide or BoNT/A $H_c$ (FIG. 9d). These data substantiate the fidelity of the synthetic peptides in vivo in mimicking the immunogenicity of the naturally processed BoNT/A.

Taken together, the results so far suggested that the epitopes detected by MAbs were good immunogens and, therefore, the peptides were used as candidates in a preliminary vaccine trial. Mice were immunized with a single peptide, combination of peptides, or BoNT/A $H_c$, and challenged 3 weeks after the final immunization with BoNT/A (Table 5). The highest dose was most effective in eliciting high antibody titers for all peptides (data not shown). All mice that were vaccinated with 2 or 10 μg of peptide and challenged with 10 $LD_{50}$ of BoNT/A died. Mice immunized with peptide 1 were not protected against any lethal challenge doses. Vaccination with peptide 2 resulted in 40% survival when mice were given 10 or 40 μg and challenged with 5 or 10 $LD_{50}$, respectively. Slightly more protection was afforded when combination of peptide 1 and 2 were used in the vaccination protocol. This finding is consistent with the hypothesis that these two peptides may be a part of a single protective epitope on the Hc of BoNT/A. All mice vaccinated with BoNT/A $H_c$ were completely protected against challenge. Mice that received control peptide, then challenged with 5 or 10 $LD_{50}$ of BoNT/A were all killed. No noticeable effects on the outcome of these experiments were observed when peptides were conjugated to KLH, or administered with other adjuvants (data not shown).

TABLE 5

Vaccine potential of 25-mer designed peptides

| Immunizing[a] agent | Dose[b] | Challenge[c] (μg/mouse) | Live/Total[d] (LD50) |
|---|---|---|---|
| Peptide 1 | 2 | 10 | 0/5 |
| | 10 | 10 | 0/5 |
| | 40 | 10 | 0/5 |
| | 10 | 5 | 0/5 |
| Peptide 2 | 2 | 10 | 0/5 |
| | 10 | 10 | 0/5 |
| | 40 | 10 | 2/5 |
| | 10 | 5 | 2/5 |
| Peptide 1 + 2 | 2 | 10 | 0/5 |
| | 10 | 10 | 0/5 |
| | 40 | 10 | 3/5 |
| | 10 | 5 | 3/5 |
| BoNT/A Hc | 2 | 1,000 | 5/5 |
| Control Peptide | 40 | 5 | 0/5 |

[a]Mice were vaccinated i.p. and boosted at 3, 6, and 9 weeks.
[b]Immunizing dose of each immunogen.
[c]Mice were challenged with BoNT/A 3 weeks after the final boost.
[d]Lethality was recorded 7 days after the challenge dose.

One of the goals of this study was to validate the predictive abilities of molecular modelling studies that used theoretically derived predictions of secondary structure and solvent accessibility of the residues to identify surfaces that interact with MAbs. We reasoned that careful attention to the kinetics of MAbs may permit us to combine the benefit of modelling with the high-affinity neutralizing MAbs to identify selected regions that may play a critical role in forming PPADS. To substantiate further this logic, low-affinity MAbs that recognize the peptides or BoNT/A $H_c$ are being tested for their ability to protect mice against BoNT/A.

There is some evidence from this study and previously published data that significant discontinuity may exist in neutralizing epitopes within BoNT/A (Dertzbaugh and West, 1996, supra). In addition, epitope mapping of these MAbs by using a constrained-peptide display library supports the existence of discontinuous epitopes within BoNT/A (M. Segall and S. Bavari, unpublished data). Therefore, we believe a single, short-peptide vaccine may not be feasible for generating protective immunity against BoNT/A. However, because a single MAb with a very high affinity can block the lethality of BoNT/A, it might be possible to design a vaccine with a combination of two peptides.

Unlike BoNT/A H$_c$, the highest titers to the peptides were detected after the third boost. This may be due to unwanted degradation of the peptides before reaching receptive major histocompatibility complex class II molecules. In hope of increasing the immunogenicity of peptides, we are currently developing delivery methods to protect better the peptides from degradation in acidic compartments of antigen-presenting cells. To increase efficiency of forming complexes with major histocompatibility complex class II molecules, peptides are being engineered with various signal motifs that should more efficiently deliver the peptides to peptide-loading compartments of antigen-presenting cells.

In this targeted survey of two peptides, we have not yet explored details of the kinetics of association and dissociation for peptide and MAbs. However, the initial data suggest there is a correlation between the level of MAb binding to H$_c$ of BoNT/A, and the effectiveness of the MAb peptide complex formation (D. Pless and S. Bavari, unpublished observations). A survey of amino acid substitutions will allow us to monitor the behavior of the two peptides and identify key amino-acid residues, particularly at solvent-exposed positions, that could alter binding to MAbs. This type of approach may further help to boost the efficacy of the peptides.

In conclusion, our study demonstrated that robust molecular modelling studies that predict secondary structure and locate highly solvent-exposed residues combined with very high-affinity neutralizing MAbs may be used to identify PPADs. This type of approach can be used as a viable alternative to the expensive and time-consuming methods of identifying neutralizing epitopes by synthesizing overwhelming numbers of long peptides.

What is claimed is:

1. Monoclonal antibody 6C2-4, produced by the hybridoma cell line deposited with the American Type Culture Collection under accession number ATCC PTA-970.

2. A composition comprising the monoclonal antibody of claim 1.

3. A pharmaceutical composition comprising the monoclonal antibody of claim 1.

4. The continuous hybridoma cell line deposited with the American Type Culture Collection under accession number ATCC PTA-970.

5. A method for detecting BoNT/A said method comprising:
   (i) incubating a sample with an effective amount of one or more monoclonal antibody against BoNT/A comprising 6C2-4 produced by the hybridoma cell line deposited with the American Type Culture Collection under accession number ATCC PTA 970, under conditions which allow the formation of an antibody-BoNT/A complex; and
   (ii) detecting the antibody-BoNT/A complex wherein the presence or absence of the complex indicates the presence or absence of BoNT/A in the sample.

6. A method for detecting BoNT/A according to claim 5 wherein, said sample is water, a biological sample, an environmental sample, or a food product.

7. A kit for detecting BoNT/A in a sample, said kit comprising:
   (1) a container containing monoclonal antibody 6C2-4 produced by the hybridoma cell line deposited with the American Type Culture Collection under the accession number ATCC PTA-970; and, optionally
   (2) instructions for using the antibody for the purpose of binding to BoNT/A to form an immunological complex and detecting the formation of the immunological complex such that presence or absence of immunological complex correlates with presence or absence of BoNT/A in said sample.

8. A method for capturing BoNT/A from a sample, said method comprising contacting said sample with the monoclonal antibody 6C2-4, produced by the hybridoma cell line deposited with the American Type Culture Collection under the accession number ATCC PTA-970, and isolating the complex formed between the BoNT/A in the sample and the monoclonal antibody.

9. The method according to claim 8 wherein said sample is selected from the group consisting of: a biological sample, an environmental sample and a food product.

* * * * *